United States Patent
Kössler et al.

(10) Patent No.: US 7,378,117 B2
(45) Date of Patent: May 27, 2008

(54) METHOD FOR THE PRODUCTION OF POTATO JUICE PRODUCTS BY MEANS OF FOOD TECHNOLOGY

(75) Inventors: Peter Kössler, Mariapfarr (AT); Norbert Fuchs, Mariapfarr (AT)

(73) Assignee: Vis-Vitalis Lizenz-und Handels GmbH, Anif (AT)

(*) Notice: Subject to any disclaimer, the term of this patent is extended or adjusted under 35 U.S.C. 154(b) by 545 days.

(21) Appl. No.: 10/511,072

(22) PCT Filed: Apr. 17, 2003

(86) PCT No.: PCT/AT03/00114

§ 371 (c)(1),
(2), (4) Date: Oct. 12, 2004

(87) PCT Pub. No.: WO03/086102

PCT Pub. Date: Oct. 23, 2003

(65) Prior Publication Data

US 2005/0208198 A1    Sep. 22, 2005

(30) Foreign Application Priority Data

Apr. 18, 2002 (AT) ............................... A 601/2002

(51) Int. Cl.
*A23L 2/02* (2006.01)
*A23L 2/08* (2006.01)

(52) U.S. Cl. ................. 426/74; 426/478; 426/481
(58) Field of Classification Search .............. 426/74, 426/478, 481
See application file for complete search history.

(56) References Cited

U.S. PATENT DOCUMENTS 3,342,719 A * 9/1967 Chen et al. ................. 204/633
6,440,222 B1 * 8/2002 Donovan et al. ............. 127/55

FOREIGN PATENT DOCUMENTS

| DE | 197 55 426 | 6/1999 |
| GB | 1 520 738 | 8/1978 |
| JP | 53115660 | 10/1978 |
| JP | 58051880 | 3/1983 |
| JP | 03239701 | 10/1991 |

OTHER PUBLICATIONS

XP-002255668, Jul. 10, 1979, Abstract.

* cited by examiner

*Primary Examiner*—Helen Pratt
(74) *Attorney, Agent, or Firm*—Fulbright & Jaworski LLP

(57) ABSTRACT

The invention relates to a method for the production of potato juice based products by means of food technology, characterized by the following steps; preparing the squeezed potato juice, filtering off the fibers or starch residues by means of a microfilter, preferably ultrafiltration the filtrate, electrodialysis of the microfiltrate or the ultrafiltrate and optionally, drying the electrodialysate by adding carrier substances containing silicates.

32 Claims, 5 Drawing Sheets

METHOD FOR THE PRODUCTION OF POTATO JUICE PRODUCTS BY MEANS OF FOOD TECHNOLOGY

The invention relates to a method for the food-technological preparation of potato juice products.

This application is a national phase application under 35 U.S.C. §371 of International Application No. PCT/AT03/00114 filed 17 Apr. 2003, which claims priority to Austrian Application No. A 601/2002 filed 18 Apr. 2002, the contents of both of which applications are incorporated herein by reference in their entirety.

Being a vital system, the acid-base balance of the human organism is aimed to permanently eliminate from the metabolism the intracellularly incurred excess of acids. While the $CO_2$ incurred at a daily amount of around 13,000 mmol is secreted as a volatile acid through respiration, additional 40 to 60 mmol of protons from nonvolatile acids are incurred every day. These acids (and even $CO_2$) are regulated in a healthy organism via various buffer systems with a view to keeping largely constant the pH in the extracellular space and in blood. Respiratory or metabolic deviations from physiologic pH ranges (acidoses or alcaloses) constitute life-threatening conditions and, therefore, have to be appropriately therapized in the context of acute medicine.

On the other hand, "latent connective-tissue acidose" is being discussed as less life-threatening, yet as an "environment-related cause" of numerous diseases, constituting a relative hyperacidity of the interstitium and an overload on the basic buffer capacities of the connective tissue by endogenously and/or exogenously incurred metabolic acids. Diseases of the gastrointestinal tract, liver and pancreas disorders, cardiovascular disorders, bronchial asthma, diabetes mellitus, migraine, osteoporosis, rheumatic diseases, loss of hair, immunologic diseases like cancer, renal insufficiency, skin diseases, neurological symptoms, vomiting of pregnancy, circulatory disturbances as well as limited performance in sports and heavy labour are associated with latent connective-tissue acidoses.

*Solanum tuberosum* (potato) was originally imported into Europe from South America and over time has become one of the most important staple foods here. The potato tuber is above all appreciated for its content of easily digestible starch, its high-grade amino acid pattern and its content of natural vitamins. Less known is its content of electrolytes (potassium, magnesium and calcium ions), which are present in the potato tuber mainly in the form of organic salts. On account of its high content of "basic or base-forming" electrolytes, the potato belongs to the base-forming staple foods. Base-forming foods, on the one hand, serve to reduce the endogenous output of nonvolatile acids and, on the other hand, serve to neutralize incurred metabolic acids and supply them to renal excretion.

However, during the procedure of processing potatoes to (pressed) potato juice, several disturbing processes can be found and must be controlled: Thus, phenol oxidases are able to oxidize to brownish-grey polymers phenolic compounds present in potato juice, such as anthocyanidins, flavons and flavonols, thus leading to an irritating enzymatic discoloration of the product.

Furthermore, the food-scientifically important ingredients of potatoes are also partially considerably reduced in terms of activity by storage: Thus, also the contents of vitamin C in potatoes are largely dependent on the harvest dates and storage conditions; for instance, a potato which is boiled without peels in March after six months of storage contains no more than 2 to 3 mg vitamin C per 100 g, which corresponds to no more than approximately one tenth of the original fresh value.

It was, therefore, the object of the present invention to provide a food-technologically applicable method for preparing potato juice products, by which a product having a high content of basic or base-forming electrolytes will be obtained, which product is stable and, in addition to exhibiting a high electrolyte content, also contains a high portion of dissolved organic carbon compounds.

The present invention, therefore, relates to a method for the food-technological preparation of potato juice products, which is characterized by the following steps:
provision of a pressed potato juice
separation of fiber or starch residues by filtration through microfilters
preferably ultrafiltration of the filtrate
electrodialysis of the microfiltrate or ultrafiltrate, respectively, and
optionally drying of the electrodialysate under the addition of silicate-containing carrier substances.

By said combination of method steps in the method according to the invention it was feasible in a surprising manner to efficiently separate the electrolytic portion of fresh potato juice from the main components of the potato tuber, namely carbohydrates and starch (around 86% of the dry substance), as well as from proteins and free amino acids (around 12-13% of the dry substance). In doing so, the pressed potato juice (or fresh potato juice) is provided first. The way in which this juice is provided is not critical; the person skilled in the art may choose among numerous, even large-scale methods. Suitable bench-scale methods are known too. It is, for instance, possible to mechanically crush washed and peeled potatoes and extract them in commercially available juice extractors. Solids forming during juice production and, in particular, potato starch as the main portion, as a rule, are initially separated by simple sedimentation (usually under cooling, for instance, to 4° C.). According to the invention, the pressed potato juice thus forming is initially purified from possibly still present fine residues such as fiber or starch residues by microfiltration known per se.

After this, the provision of an ultrafiltration is particularly suitable in the method according to the invention to prevent problems caused by membrane obstruction, i.e., so-called fouling phenomena, during subsequent electrodialysis. Ultrafiltration serves to separate higher molecular components already prior to carrying out electrodialysis.

The microfiltration provided according to the invention and the preferred ultrafiltration in the present method are followed by the step of electrodialysis.

Unlike microfiltration or ultrafiltration, where the dissolved substances are separated exclusively according to their particle sizes irrespective of their chemical and electrochemical properties, electrodialysis causes a charge-dependent separation of substances. Electrodialysis is a membrane technique by which all ionogenic components are affected by an electric field. They can, thus, be specifically separated according to their charges. In doing so, the different ions can be separated into cations and anions by the aid of selective ion exchange membranes with an electric potential gradient acting as the driving force. Due to the electric potential applied, the dissolved ions migrate through the membranes towards the respective electrode in a manner that a diluted solution, the so-called diluate, will remain on the one side of the membrane and the ions will be enriched in the so-called concentrate on the other side.

In a preferred manner, a membrane stack is used, the individual membranes being separated by spacers and the thus formed spaces being separated from one another and from the electrode chamber by means of sealing frames. The alternate use of cation and anion exchange membranes results in the enrichment of ions in the so-called concentrate cycle and an accordingly large decrease of charge carriers in the so-called diluate cycle.

JP 53-115660 A relates to a method for treating a juice comprising proteins, inorganic salts and similar ingredients, whereby the juice is passed through an inverse feed-through separator and a microfilter. In doing so, a protein-enriched juice fraction is obtained, which is depleted of inorganic salts. No mention is made either that said method can be used for the production of potato juice or potato juice products or that an electrodialysis of the obtained juice is carried out. Furthermore, no ultrafiltration or drying of the electrodialysate upon addition of silicate-containing carrier substances is addressed in this document.

The depletion of inorganic salts according to JP 53-115660 A by contrast even constitutes an effect exactly opposite to that reached by the method according to the invention, by which technological method steps are realized in series in a manner that the (basic and base-forming) electrolytes (to which also inorganic salts belong) from potatoes will be enriched. Thus, not only the technology of the cited method differs largely from the method according to the invention, but also the effect obtained by said method is exactly opposite to that envisaged by the method according to the invention.

JP 58-051880 A relates to a method for producing fruit juices, in which the juice is passed over an ultrafiltration membrane. That method is, however, not described as being applicable to producing potato juice. Besides, filtration through microfilters and subsequent electrodialysis of the microfiltrate is not mentioned and the drying of the electrodialysate under the addition of silicate-containing carrier substances is not mentioned either.

The object of the method according to JP 58-051880 A consists in specifically fractionating juices (and, in particular, fruit juices) by ultrafiltration in a manner that the sedimentation of suspended matter will be minimized so as to obtain readily soluble fruit juice concentrates. Also that method is, therefore, not aimed at recovering basic and base-forming electrolytes from potatoes (which do definitely not rank among the fruits to be used under the definition of the method described there).

Finally, JP 03-239701 A relates to a method for producing potato starch, by which a potato starting material (ground potato milk) is deproteinized by the aid of anion exchangers comprising tertiary amine or quaternary ammonium groups. By contrast, the method according to the present invention is not directed to a method for producing potato starch, but to a method for producing potato juice products, in which exactly that protein portion which is to be removed in the above document must be retained in order to enable the food-physiological targets to be realized by the potato juice products according to the invention. That Japanese application thus clearly leads into a completely different direction, since it is mainly the starch fraction which is separated in addition to proteins according to the present method in order to enrich the content of basic electrolytes and trace elements to the optimum degree, whereas the method disclosed in that document merely serves to recover liquid potato starch concentrates as nutritional key substances intended to aromatize foods and confer consistency on them.

After this, the electrodialysate obtained according to the invention, being a food-technological potato juice may, if desired, be immediately completed to appropriate food products or may be further processed or stored—optionally as an intermediate product. Yet, drying of the juice is recommended for storage purposes. In order to avoid the formation of an amorphous mass during that drying process, carrier substances are preferably added during drying, which should, of course, be qualified from a food-technological aspect, i.e., not induce any undesired properties in foodstuffs. In this context, silicate-containing carrier substances and, in particular, highly disperse silicates containing silicon dioxide have proved to be particularly useful. By highly disperse silicates, silicate-containing carrier substances having large surface areas (e.g., a surface area of more than 50 $m^2/g$, more than 100 $m^2/g$ or more than 150 $m^2/g$) such as, e.g., Aerosil 200 (surface area 200 $m^2/g$) or Aerosil 380 (surface area 380 $m^2/g$) are understood.

According to a preferred embodiment, stabilizers are added to the pressed potato juice. It is beneficial to add the same already after or during pressing. In this context, the use of lemons or (pressed) lemon juice or lemon juice products has proved particularly suitable, because, being natural antioxidants, these are able to prevent undesired enzymatic activities in the potato juice, which are primarily caused by oxidases. In the context of the method according to the invention, very good results have also been achieved with ascorbic acid, black currant juice, elderberry flower extract, sallow thorn juice, whole lemons or whole red peppers. Among the particularly natural antioxidants that may be used as stabilizers, lemon juice or lemon juice products are particularly preferred as already mentioned, yet the optimization of the stabilizer in each individual case will also depend on the specific potato variety or type of growth and storage.

In a preferred manner, the pressed potato juice is made from potatoes having a ratio of base-forming to acid-forming components of at least 1.5 and, preferably, more than 3.5. This ratio can be readily determined by every person skilled in the art through simple analytics of the starting material. According to the invention, pressed potato juices from the varieties Desiree and Ackersegen are particularly preferred. Other preferred varieties include Bintje, Desiree, Ostara and Planta. Yet, also other hard-boiling, mainly hard-boiling or mealy-boiling potatoes are well apt for the method according to the invention. As a rule, the starting products should, however, be previously examined primarily for their (basic) electrolyte contents and selected—also batch-wise—while taking into account the abovementioned ratio of base-forming to acid-forming components. Said ratio is often characterized by way of the calcium/phosphorus ratio, yet it is more precise to determine the quotient of molar concentrations of acid-forming components divided by the sum of molar concentrations of base-forming components. Acid-forming components include sulfate, phosphate, chloride, nitrate, malate, lactate, tartrate, citrate, isocitrate and L-ascorbate. Base-forming components include potassium, magnesium, calcium, sodium, ammonium, iron, zinc, manganese, copper, selenium, nickel and chromium.

As already mentioned, potential problems (fouling, membrane obstruction, . . . ) involved in electrodialysis can be avoided by providing an ultrafiltration step. Preferably, an ultrafilter having an exclusion limit of below 100,000 Da, preferably below 10,000 Da and, in particular, approximately 1,000 Da is used, wherein an overpressure of preferably 1.1 to 10 bar and, in particular, approximately 2 bar is usually applied.

According to the invention, the use of low-diffusion membranes has proved particularly suitable in electrodialysis, thus largely avoiding the contamination and swelling of the electrodialytic membranes (even without ultrafiltration) as well as possible fouling processes.

As already mentioned, the pressed potato juice according to the invention can be immediately processed in a food-technological manner. Storage or transportation in the liquid state is, however, not always desired with larger (industrial) quantities such that the method according to the invention is preferably followed by a drying procedure. Since the conventional drying of potato juice merely results in an amorphous mass difficult to handle on an industrial scale, highly disperse silicon dioxide is preferably added during the drying process according to the invention.

In a preferred manner, the potato juice product obtained and optionally dried is supplemented with one or several additional agents, preferably at least one additional vegetable or fruit juice, one or several stabilizers and, in particular, natural antioxidants, one or several particularly natural flavoring or coloring agents, one or several thickening agents, reconstitution or electrolytic agents or combinations of said agents. Furthermore, the dried potato product may also be supplemented with vitamins, mineral substances, trace elements or secondary plant substances in any quality and quantity, individually or in combination. Reconstitution agents serve the complete and rapid reconversion into the liquid state; electrolytic agents impart additional electrolytes on the potato juice powder to be reconstituted.

Drying is preferably effected by spray-drying or drum-drying. An advantage of the addition of silicon dioxide preparations also consists in that conventional, industrially applicable drying plants can be employed.

According to another aspect, the present invention also relates to a potato juice product which is obtainable according to the method of the invention.

Depending on the concentration of the juice or content in the starting material, respectively, the potato juice product according to the invention preferably contains 1000 mg/l or more, preferably 2000 mg/l or more and, in particular, 4000 mg/l or more, of organic components, preferably determined as non-purgeable organic carbon.

A particularly preferred potato juice product according to the invention is characterized in that it has a ratio of baseforming components to acid-forming components of at least 2.5, preferably above 4 and, in particular, above 6.

Furthermore, the present invention also relates to the use of potato juice products according to the invention having basic or base-forming electrolytes for (the production of an agent for) regulating the acid/base balance in human or animal organisms. In that case, the agent may be administered in suitable doses to maintain the acid/base balance in humans or animals.

BRIEF DESCRIPTION OF THE DRAWINGS

The invention will be explained in more detail by way of the following examples as well as the drawing figures, to which it is, of course, not to be limited.

1. Stabilization Tests

1.1 Materials

Figure 1:
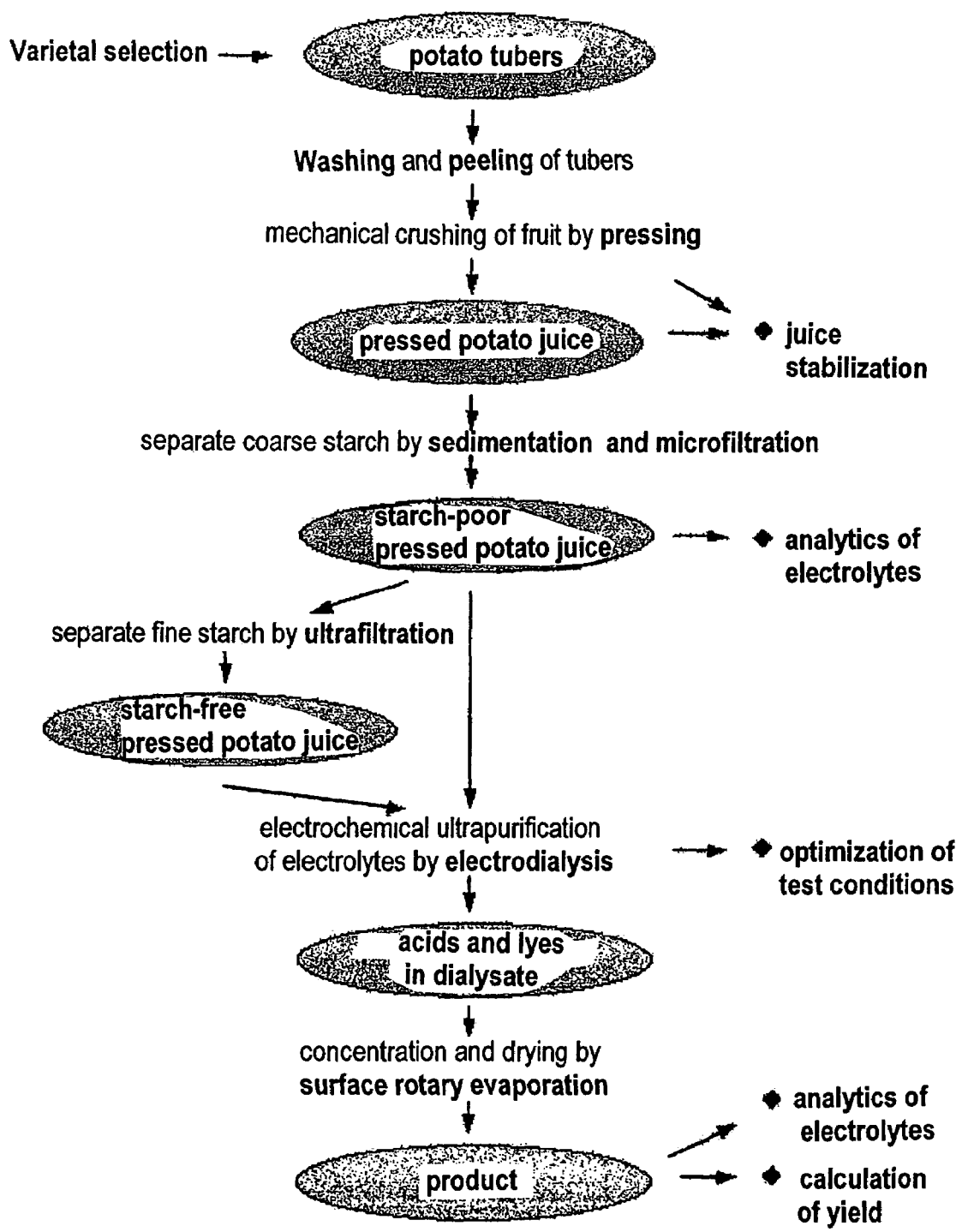
FIG. 1 is a survey of a preferred method according to the invention.

Departing from the conventional approach to use approved antioxidants for the stabilization of pressed potato juice, it was investigated whether the addition of selected plant materials (fruits, vegetables) was suitable to inhibit phenoloxidase activity. The selection of such additives was made in compliance with health-relevant, ecological, technological and economic criteria.

To the extent available, fruits/vegetables from certified organic farming were used; where COF-qualities were not available, standardized commercially available plant juices (COF) were partly chosen.

Potato Sample Material

| | |
|---|---|
| AGATA | Austrian new potatoes from organic farming, harvest 2001, hard-boiling |
| FRIESLANDER | Austrian new potatoes from organic farming, harvest 2001, mainly hard-boiling |
| BINTJE | from Austrian organic farms, harvest 2000, mainly hard-boiling |

Substances Used in Stabilization Tests
   Octyl gallate E311
   Ascorbic acid E300
   $CO_2$ gassing
   pressed broccoli juice
   elderflower extract (standardized commercially available product)
   pressed cabbage juice
   green pepper pressed juice
   whole red pepper
   sallow thorn juice (standardized commercially available product)
   black currant juice (standardized commercially available product)
   whole lemon
   lemon juice Implements
Potato peeler stainless steel
Juice extractor centrifuge ELIN
Standard glass eprouvettes, parafilm
Normalized color palette
Canon digital camera, halogen lamp

1.2 Methods

Stabilization Tests by Additives After Pressing Procedure

Potato juice was obtained from the peeled, washed potatoes by means of a juice extractor centrifuge at a rapid sample material throughput. Immediately after this, the juice was transferred into the test vessels and supplemented with the respective stabilizing additive at different concentrations.

Stabilization Tests by Additives During Pressing Procedure

The peeled, washed and coarsely pieced (halved to quartered) potatoes were mixed with the respective additive (vegetable pieces of around 1 $cm^3$) as homogenously as possible. Liquid additives were uniformly dosed in during centrifuge extraction. The potato juice+additive mixtures were recovered at rapid flow rates. The samples were immediately transferred into eprouvettes.

Test Procedure

The potato juice+additive mixtures are provided in closed glass eprouvettes of identical size and identical quality.
The color values of the potato juice+additive mixtures as well as the reference samples (without additives) were documented by way of a color table comparison at laboratory lighting as well as by means of a digital camera at halogen lamp light.
Taking of the color values: First immediately after sample preparation, then at daily intervals
Observation period: 1 week Evaluation The color values at the beginning of the test were compared to the values observed after one week.

| | | | |
|---|---|---|---|
| +++ | no or just very slight color change | − | insignificant inhibition of discoloration |
| ++ | medium discoloration | −− | strong discoloration |
| + | still significant inhibition of discoloration | −−− | very strong discoloration (blackish-brown) |

1.3 Results of Stabilization Tests

The results of the stabilization tests are summarized in the following Table 1.

Stablization Test Results

2. Varietal Selection

Since it is to be anticipated that different potato species (mealy, hard-boiling, etc.) and regionally specific particularities will considerably influence the distribution pattern of the ingredients, different varieties cultivated in Austria were examined in view of the recoverable electrolytes potassium, magnesium, calcium, sodium, iron, zinc, manganese, copper, selenium, nickel, chromium, ammonium, the inorganic anions sulfate, phosphate, chloride and nitrate, as well as the organic anions ascorbate, malate, lactate, tartrate, citrate and isocitrate.

2.1 Potato Sample Material

TABLE 2

| Code | Solanum tuberosum | Origin | Harvest | Type |
|---|---|---|---|---|
| L1 | Ostara | Lungau | 2000 | mainly hard-boiling |
| L2 | Desiree | Lungau | 2000 | mainly hard-boiling |
| S3 | Planta | Stainz | 2000 | mainly hard-boiling |
| S4 | Desiree | Stainz | 2000 | mainly hard-boiling |
| B5 | Bintje | Gratkorn | 2000 | mainly hard-boiling |
| 01 | Ostara | Lungau | 2001 | mainly hard-boiling |

TABLE 1

Stabilization Tests by Additives

| AFTER pressing procedure | Additives %(w/w) | Remarks | Values after 1 week | Interpretation |
|---|---|---|---|---|
| Ascorbic acid E300 | 0.01% to 2.5% | | +++ | => shows good stabilization |
| Lemon pressed juice | 0.01% to 10% | brightens | ++/+++ | => shows good stabilization |
| Black currant juice | 0.05% to 10% | self-coloration | + | Stabilization potential present |
| Elderflower extract | 0.05% to 10% | | + | => Stabilization potential present |
| Sallow thorn juice | 0.05% to 10% | flocculation self-coloration | + | => Stabilization potential present |
| Octyl gallate E311 | 0.01% to 2.5% | | − | => slight stabilization potential |
| Pressed juice green pepper | 0.05% to 10% | self-coloration | − | => Tests with red pepper |
| Pressed juice from broccoli | 0.05% to 10% | self-coloration | − | => was not further pursued |
| Pressed juice from cabbage | 0.05% to 10% | self-coloration | − | => was not further pursued |
| DURING pressing | Additives | | | |
| Whole lemon (COF, untreated!) | 5% to 10% | brigthens | +++ | => shows excellent stabilization potential; optimization with regard to minimum concentration used |
| Elderflower extract | 5% to 10% | | +++ | => shows excellent stabilization potential; optimization with regard to minimum concentration used |
| Black current juice | 5% to 10% | self-coloration | ++/+++ | => shows good stabilization potential; "native" raw material; self-coloration to be considered |
| Sallow thorn juice | 5% to 10% | strong flocculation, self-coloration | ++/+++ | => shows good stabilization potential; slight self-coloration and strong flocculation to be considered |
| Whole red pepper | 5% to 10% | self-coloration | ++/+++ | => shows good stabilization potential; strong self-coloration to be considered; nitrate drag-in !? |
| Potato juice Reference samples "stored" | — | | −− | => strong discoloration within extremely short time - already during pressing |
| Potato juice Reference samples "farm-fresh" | — | | +/− | => Pressed juice from farm-fresh potatoes shows relatively good stability under cooling and exclusion of air |

TABLE 2-continued

| Code | Solanum tuberosum | Origin | Harvest | Type |
|------|-------------------|--------|---------|------|
| D1 | Desiree | Lungau | 2001 | mainly hard-boiling |
| A1 | Ackersegen | Lungau | 2001 | mealy |

2.2 Sample Material Quality

All of the sample material used complied at least with the criteria required for table potatoes pursuant to Federal Gazette No. 76/1994 as amended by Fed. Gaz. 240/1997, ordinance issued by the Federal Ministry of Agriculture and Forestry on quality classes for table potatoes, i.e., fresh appearance, roughly looking healthy, mainly hard-boiling or mealy. According to §3 of this ordinance, the potatoes used in this case were:
1. intact,
2. healthy and, in particular, free of wet, brown and dry rot, surface scrab exceeding 25% of the tuber surface, a scrab depth exceeding 10% of the tuber surface, heat or frost damage, iron spots, hollow or black cores, heavy knob formation, strong glassiness, heavy pimples and intense black spots,
3. clean, which meant nearly free of earth or sand,
4. solid, which meant not flabby or shrivelled,
5. free of abnormal external moisture,
6. free of strange smell or taste,
7. free of heavy damage, nibbling sites or heavy squeezing,
8. free of tubers turned markedly green, and
9. free of deformed tubers (secondary tuber formation, sprouted tubers, etc.).

Moreover, the packed pieces were free of any foreign matter like soil, sand or loose germs, and basically peel-firm.

In addition, the used potatoes exhibited the following constitutional characteristics (class I):

The potatoes were varietally true. The following defects were allowed though:
a) slight greenish coloration on no more than ⅛ of the tuber surface;
b) slight superficial damage removable by regular peeling;
c) damage or black spots reaching no deeper than 5 mm and removable by loosing no more than 10% of the tuber weight; and
d) shoots having lengths of no more than 3 mm.

The classification of table potatoes according to their boiling types was effected as follows:
1. Hard-boiling potatoes:
   Agata*), Ditta, Evita, Exquisa, Julia, Linzer Delikatess, Naglemer Kipfler, Nicola, Novita, Punika, Sieglinde, Sigma, Sonja
2. Mainly hard-boiling potatoes:
   Accent, Adora*), Berber*), Bettina, Bintje, Bionta, Celeste*), Christa*), Cinja, Desiree, Erstling*), Frieslander*), Gina*), Goldsegen, Impala*), Isola, Jaerla*), Jetta, Linzer Gelbe, Minerva*), Ostara*), Planta, Platina, Quarta, Romina, Rosella, Rubinia*), Salenta, Sirtema*), Timate, Ukama*).
3. Mealy-boiling (mealy) potatoes:
   Ackersegen, Agria, Ares, Asterix, Aula, Cosima, Donald, Erntestolz, Fambo, Hermes, Mondial, Remarka, Russet Burbank, Satuma, Signal, Solara, Treff, VanGogh, Welsa.
*) very early ripening potatoes 2.3 Methods An extensive analytics of the ingredients determining the value of the product according to the invention was carried out for varietal selection.

The washed and peeled potatoes were mechanically crushed and extracted in a commonly available juice extractor. The major quantity of potato starch was separated by sedimentation for several hours at +4° C. The thus obtained starch-poor pressed potato juice was examined as follows:

cations (potassium, magnesium, calcium, sodium, iron, zinc, manganese, copper, selenium, nickel and chromium) were quantified after an acid digestion by sulphuric acid, by means of ICP-MS (mass spectrometry with inductively coupled plasma);

ammonium was photometrically detected by the aid of Nessler's reagent after filtration;

inorganic anions (sulfate, phosphate, chloride and nitrate) were detected by means of IC (ion chromatography) and conductivity measurement after filtration;

organic anions (malate, lactate, tartrate, citrate and isocitrate) were likewise detected by means of IC (ion chromatography) and conductivity measurement after filtration;

ascorbate was photometrically determined before and after enzymatic oxidation with ascorbate oxidase;

as the summation parameter for organic components, the DOC (dissolved organic carbon) was determined as NPOC (non-purgeable organic carbon).

Departing from the technique of characterizing the acid- or base-forming properties of foodstuffs via the calcium/phosphorus ratio to be frequently found in literature, that calculation variant was extended to the summation values from analytics.

For evaluation purposes, the molar concentrations of the acid-forming anions were based on those of the base-forming cations. The thus obtained quotient was applied as the decisive criterion in selecting the varieties.

$$Q = \frac{\sum \text{of molar concentrations of acid-forming components}}{\sum \text{of molar concentrations of base-forming components}}$$

Values <1 are allocated the physiological property "acid-forming" and values >1 the physiological property "base-forming". The higher the value the more strongly base-forming the sample.

2.4 Results from Examinations of Selected Potato Varieties

The first examinations were carried out on the potato cultivars Ostara and Desiree originating from Lungau, Planta and Desiree from Stainz and Bintje from Gratkorn, from the 2000 crop in spring 2001, i.e., after a storage time of around six months. The results of these examinations are summarized in the Tables on the following pages (Tables 2a, b, c).

Furthermore, the varieties Ostara, Desiree and Ackersegen, reaped in Lungau, were also examined immediately after the harvest in 2001.

TABLE 2a

|  | mg/mmol | L1 Ostara Harvest 2000 mg/l | mmol/l | L2 Desiree Harvest 2000 mg/l | mmol/l | S3 Planta Harvest 2000 mg/l | mmol/l | S4 Desiree Harvest 2000 mg/l | mmol/l | B5 Bintje Harvest 2000 mg/l | mmol/l |
|---|---|---|---|---|---|---|---|---|---|---|---|
| Sulfate | 96.06 | 1190 | 12.39 | 702 | 7.31 | 770 | 8.02 | 663 | 6.90 | 942 | 9.81 |
| Phosphate | 94.97 | 791 | 8.33 | 796 | 8.38 | 689 | 7.25 | 592 | 6.23 | 811 | 8.54 |
| Chloride | 35.45 | 244 | 6.88 | 94 | 2.65 | 151 | 4.26 | 178 | 5.02 | 500 | 14.10 |
| Nitrate | 62.01 | 100 | 1.61 | 43 | 0.69 | 125 | 2.02 | 56 | 0.90 | 66.5 | 1.07 |
| Malate | 132.10 |  |  |  |  |  |  |  |  |  |  |
| Lactate | 89.08 |  |  |  |  |  |  |  |  |  |  |
| Tartrate | 148.10 |  |  |  |  |  |  |  |  |  |  |
| Citrate | 189.10 |  |  |  |  |  |  |  |  |  |  |
| Isocitrate | 189.10 |  |  |  |  |  |  |  |  |  |  |
| L-Ascorbate | 175.05 |  |  |  |  |  |  |  |  |  |  |
| Sum acid-forming |  |  | 29.21 |  | 19.03 |  | 21.55 |  | 19.06 |  | 33.52 |
| Potassium | 39.10 | 2880 | 73.66 | 2640 | 67.52 | 3200 | 81.84 | 3190 | 81.59 | 4667 | 119.36 |
| Magnesium | 24.31 | 257 | 10.57 | 252 | 10.37 | 230 | 9.46 | 257 | 10.57 | 358 | 14.73 |
| Calcium | 40.08 | 27.6 | 0.69 | 23.5 | 0.59 | 32.8 | 0.82 | 19.3 | 0.48 | 80.4 | 2.01 |
| Sodium | 22.99 | 11.8 | 0.51 | 13.4 | 0.58 | 13.1 | 0.57 | 8.6 | 0.37 | 25.9 | 1.13 |
| Ammonium | 18.04 | <0.05 | n.a. | <0.05 | n.a. | <0.05 | n.a. | <0.05 | n.a. | <0.05 | n.a. |
| Iron | 55.84 | 2.07 | 0.04 | 3.95 | 0.07 | 4.33 | 0.08 | 3.44 | 0.06 | 2.9 | 0.05 |
| Zinc | 65.30 | 2.82 | 0.04 | 2.88 | 0.04 | 3.6 | 0.06 | 2.84 | 0.04 | 5.01 | 0.08 |
| Manganese | 54.94 | 1.35 | 0.02 | 1.82 | 0.03 | 1.04 | 0.02 | 1.08 | 0.02 | 1.6 | 0.03 |
| Copper | 63.54 | 0.85 | 0.01 | 1.4 | 0.02 | 1.2 | 0.02 | 1.9 | 0.03 | 1.79 | 0.03 |
| Selenium | 78.90 | <0.002 | n.a. | <0.002 | n.a. | <0.002 | n.a. | <0.002 | n.a. | <0.01 | n.a. |
| Nickel | 58.70 | <0.05 | n.a. | <0.05 | n.a. | <0.05 | n.a. | <0.05 | n.a. | 0.058 | 0.00 |
| Chromium | 52.00 | <0.05 | n.a. | <0.05 | n.a. | <0.05 | n.a. | <0.05 | n.a. | 0.016 | 0.00 |
| Sum base-forming |  |  | 85.55 |  | 79.22 |  | 92.86 |  | 93.17 |  | 137.41 |
| Ratio |  |  |  |  |  |  |  |  |  |  |  |
| (Σbase-forming) to (Σacid-forming) |  |  | 2.93 Ostara 00 |  | 4.16 Desiree 00 |  | 4.31 Planta 00 |  | 4.89 Desiree 00 |  | 4.10 Bintje 00 |

TABLE 2b

|  | mg/mmol | O1 Ostara Harvest 2001 mg/l | mmol/l | D1 Desiree Harvest 2001 mg/l | mmol/l | A1 Ackersegen 2001 mg/l | mmol/l |
|---|---|---|---|---|---|---|---|
| Sulfate | 96.06 | 728 | 7.58 | 405 | 4.22 | 274 | 2.85 |
| Phosphate | 94.97 | 520 | 5.48 | 597 | 6.29 | 454 | 4.78 |
| Chloride | 35.45 | 514 | 14.50 | 175 | 4.94 | 95 | 2.68 |
| Nitrate | 62.01 | 137 | 2.21 | 91 | 1.47 | 14 | 0.23 |
| Malate | 132.10 | 1240 | 9.39 | 940 | 7.12 | 1400 | 10.60 |
| Lactate | 89.08 | 75 | 0.84 | 78 | 0.88 | 96 | 1.08 |
| Tartrate | 148.10 | <1 | n.a. | <1 | n.a. | <1 | n.a. |
| Citrate | 189.10 | 3300 | 17.45 | 3600 | 19.04 | 4000 | 21.15 |
| Isocitrate | 189.10 | 240 | 1.27 | 272 | 1.44 | 341 | 1.80 |
| L-Ascorbate | 175.05 | 2.4 | 0.01 | 0.8 | 0.00 | 1.9 | 0.01 |
| Sum acid-forming |  |  | 58.73 |  | 45.38 |  | 45.18 |
| Potassium | 39.10 | 2500 | 63.94 | 2390 | 61.13 | 2320 | 59.34 |
| Magnesium | 24.31 | 256 | 10.53 | 188 | 7.73 | 223 | 9.17 |
| Calcium | 40.08 | 35 | 0.87 | 45 | 1.12 | 53 | 1.32 |
| Sodium | 22.99 | 2.5 | 0.11 | 3.4 | 0.15 | 3.3 | 0.14 |
| Ammonium | 18.04 | <0.05 | n.a. | <0.05 | n.a. | <0.05 | n.a. |
| Iron | 55.84 | 0.49 | 0.01 | 0.51 | 0.01 | 1.38 | 0.02 |
| Zinc | 65.30 | 3.1 | 0.05 | 2.8 | 0.04 | 2.3 | 0.04 |
| Manganese | 54.94 | 1.35 | 0.02 | 1.42 | 0.03 | 1.44 | 0.03 |
| Copper | 63.54 | 1.3 | 0.02 | 1.1 | 0.02 | 1.3 | 0.02 |
| Selenium | 78.90 | <0.002 | n.a. | <0.002 | n.a. | <0.002 | n.a. |
| Nickel | 58.70 | 0.08 | 0.00 | 0.1 | 0.00 | 0.09 | 0.00 |
| Chromium | 52.00 | <0.05 | n.a. | <0.05 | n.a. | <0.05 | n.a. |
| Sum base-forming |  |  | 75.55 |  | 70.23 |  | 70.08 |
| Ratio |  |  |  |  |  |  |  |
| (Σ base-forming) to (Σ acid-forming) |  |  | 1.29 Ostara 01 |  | 1.55 Desiree 01 |  | 1.55 Ackersegen 01 |

TABLE 2c

|  | mg/mmol | L1 Ostara Harvest 2000 | | O1 Ostara Harvest 2001 | | L2 Desiree Harvest 2000 | | D1 Desiree Harvest 2001 | |
| --- | --- | --- | --- | --- | --- | --- | --- | --- | --- |
|  |  | mg/l | mmol/l | mg/l | mmol/l | mg/l | mmol/l | mg/l | mmol/l |
| Sulfate | 96.06 | 1190 | 12.39 | 728 | 7.58 | 702 | 7.31 | 405 | 4.22 |
| Phosphate | 94.97 | 791 | 8.33 | 520 | 5.48 | 796 | 8.38 | 597 | 6.29 |
| Chloride | 35.45 | 244 | 6.88 | 514 | 14.50 | 94 | 2.65 | 175 | 4.94 |
| Nitrate | 62.01 | 100 | 1.61 | 137 | 2.21 | 43 | 0.69 | 91 | 1.47 |
| Malate | 132.10 |  |  | 1240 | 9.39 |  |  | 940 | 7.12 |
| Lactate | 89.08 |  |  | 75 | 0.84 |  |  | 78 | 0.88 |
| Tartrate | 148.10 |  |  | <1 | n.a |  |  | <1 | n.a. |
| Citrate | 189.10 |  |  | 3300 | 17.45 |  |  | 3600 | 19.04 |
| Isocitrate | 189.10 |  |  | 240 | 1.27 |  |  | 272 | 1.44 |
| L-Ascorbate | 175.05 |  |  | 2.4 | 0.01 |  |  | 0.8 | 0.00 |
| Σ acid-forming inorganic |  |  |  |  | 29.76 |  |  |  | 16.91 |
| Σ acid-forming total |  |  | 29.21 |  | 58.73 |  | 19.03 |  | 45.38 |
| Potassium | 39.10 | 2880 | 73.66 | 2500 | 63.94 | 2640 | 67.52 | 2390 | 61.13 |
| Magnesium | 24.31 | 257 | 10.57 | 256 | 10.53 | 252 | 10.37 | 188 | 7.73 |
| Calcium | 40.08 | 27.6 | 0.69 | 35 | 0.87 | 23.5 | 0.59 | 45 | 1.12 |
| Sodium | 22.99 | 11.8 | 0.51 | 2.5 | 0.11 | 13.4 | 0.58 | 3.4 | 0.15 |
| Ammonium | 18.04 | <0.05 | n.a. | <0.05 | n.a. | <0.05 | n.a. | <0.05 | n.a. |
| Iron | 55.84 | 2.07 | 0.04 | 0.49 | 0.01 | 3.95 | 0.07 | 0.51 | 0.01 |
| Zinc | 65.30 | 2.82 | 0.04 | 3.1 | 0.05 | 2.88 | 0.04 | 2.8 | 0.04 |
| Manganese | 54.94 | 1.35 | 0.02 | 1.35 | 0.02 | 1.4 | 0.03 | 1.42 | 0.03 |
| Copper | 63.54 | 0.85 | 0.01 | 1.3 | 0.02 | 1.4 | 0.02 | 1.1 | 0.02 |
| Selenium | 78.90 | <0.002 | n.a. | <0.002 | n.a. | <0.002 | n.a. | <0.002 | n.a. |
| Nickel | 58.70 | <0.05 | n.a. | 0.08 | 0.00 | <0.05 | n.a. | 0.1 | 0.00 |
| Chromium | 52.00 | <0.05 | n.a. | <0.05 | n.a. | <0.05 | n.a. | <0.05 | n.a. |
| Σ base-forming |  |  | 85.55 |  | 75.55 |  | 79.22 |  | 70.23 |
| Ratio (Σ base-forming) to (Σ acid-forming) inorganic |  |  | 2.93 Ostara 00 |  | 2.54 Ostara 01 |  | 4.16 Desiree 00 |  | 4.15 Desiree 01 |

The results clearly indicate that, although the absolute concentration of ions increases due to a loss of water during storage, the ratio of the sum of acid-forming ions to base-forming ions, which is value-determining for the product to be developed, is not significantly affected.

The varietal selection for the continuing tests was decided in favor of the cultivar Desiree with regard to the potato material available. As to the value-determining quotient, the varieties Desiree and Ackersegen proved to be equivalent, yet the variety Desiree was preferred on account of cultivation- and harvest-related factors.

3. Recovery of Electrolytes

In principle, two alternative recovery methods for the isolation of basic electrolytes in largely pure forms according to the prior art were under discussion.

On the one hand, the exclusive separation of undesired components via the separation parameter size by applying different filtration methods (microfiltration, ultrafiltration and nano-filtration) was considered. However, since the extremely complex matrix of a pressed potato juice comprises a large number of even low-molecular—components such as, for instance, carbohydrates in different polymerization degrees (monomers, dimers, oligomers), free aminoacids, low-molecular peptides and fatty acids, a combination of two different separation methods finally turned out to be of advantage: a filtration method (ultrafiltration) using the separation parameter size followed by electrodialysis using primarily the charge of the electrolyte to be isolated, yet also permitting some sort of selection through membrane selection via the ratio of the charge based on the size (cf. FIG. 1).

3.1 Material

On account of the results from the analyses for the varietal selection, the variety Desiree was selected for the pilot tests:

Lungau table potatoes
Producer No. 22
Variety Desiree
Packing date 09.28.01
Potato store A-5580 Tamsweg 3.2 Methods 3.2.1 Preparation of Pressed Potato Juice The washed and peeled potatoes were mechanically crushed and extracted in a commonly available juice extractor. The major quantity of potato starch was separated by sedimentation for several hours at +4° C. The thus obtained pressed potato juice poor in starch was filtered in a cartridge filter having a pore size of 1 μm (microfiltration) in order to eliminate possibly present fiber and starch residues, and was used for the ultrafiltration and/or electrodialysis tests.

3.2.2 Ultrafiltration

Since the first electrodialytic tests—as described in detail in the following chapter—might involve problems due to membrane obstruction, so-called fouling phenomena, ultrafiltration of the starch-poor pressed potato juice was previously performed according to an improved electrodialytic method in order to separate higher-molecular components more efficiently.

For a pretest aimed to verify whether value-determining ions would be lost by this method step, an agitation cell available from Amicon and including a polysulfone membrane having a cut-off of 1000 Da was used at an operating pressure of below 2 bar. Since the results clearly showed that no value-determining electrolytes were lost, a pilot test was carried out, using a plate module likewise equipped with the above-mentioned polysulfone membranes having a cut-off of 1000 Da at an operating pressure of 2 bar under periodic back flushing.

3.2.3. Electrodialysis

Technical membranes used in known micro- and ultrafiltration methods separate dissolved substances exclusively according to their particle sizes irrespective of their chemical and electrochemical properties.

By contrast, electrodialysis is a membrane technique influenced by an electric field. This field acts on all ionogenic components and can be used for the separation of matter.

Also in this case, membranes serve as separating elements, yet selection is not based on the separation parameter size, but on the charge of the molecules. The different ions are separated into cations and anions by selective ion exchange membranes with an electric potential gradient functioning as the driving force. Due to the electric potential applied, the dissolved ions migrate through the membranes towards the respective electrode in a manner that a diluted solution, the so-called diluate, will remain on one side of the membrane and the ions will be enriched in the so-called concentrate on the other side.

Figure 2:
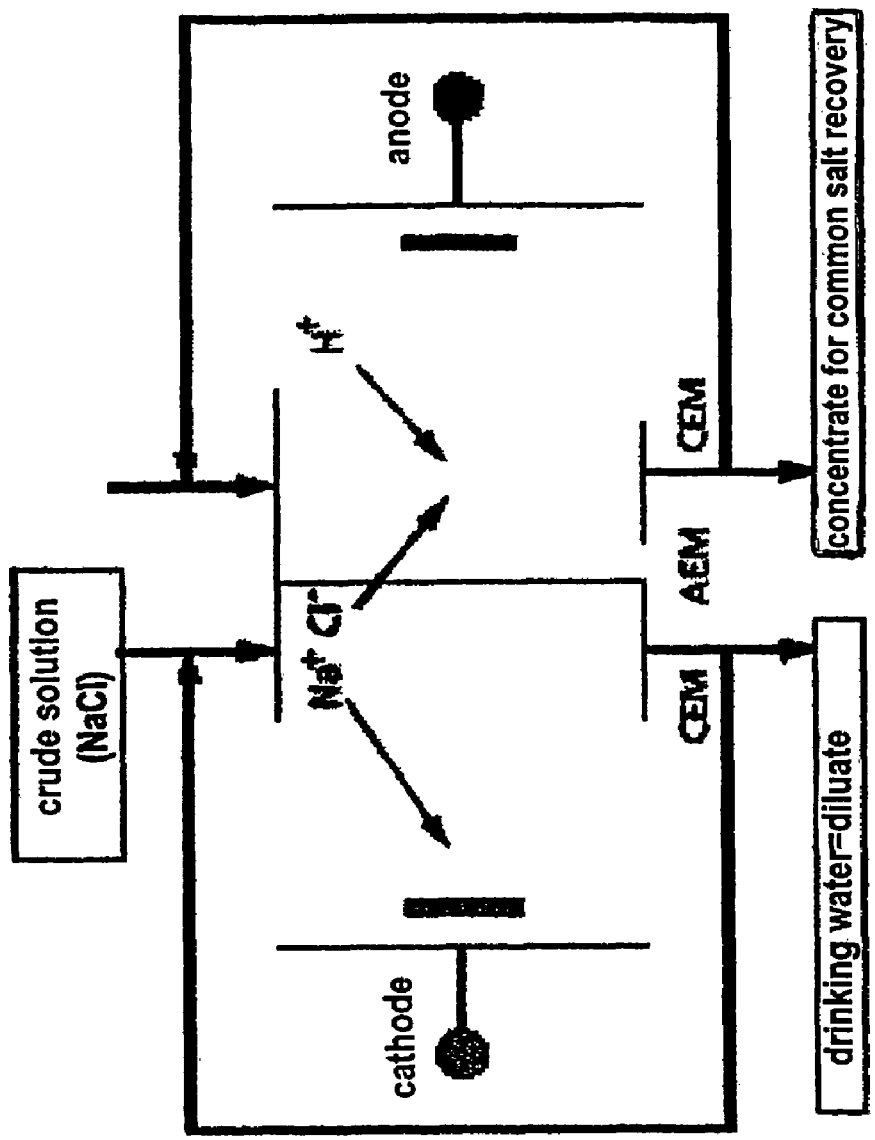
FIG. 2 illustrates the functional principle of electrodialysis, AEM denoting the anion exchange membrane and CEM denoting the cation exchange membrane.
Figure 3:
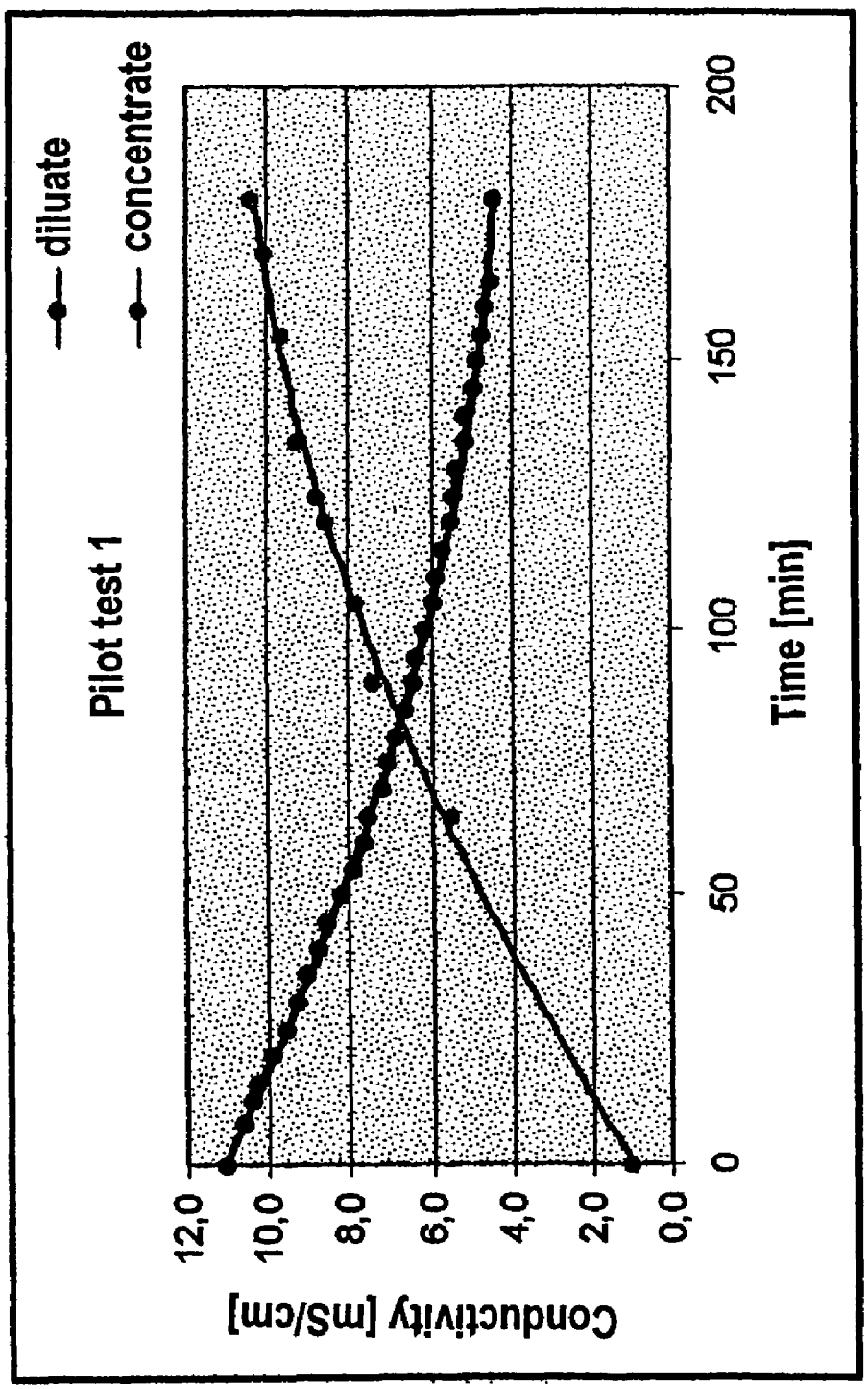
FIGS. 3 to 5 indicate the conductivities against time in the diluate and concentrate during electrodialysis in Examples 1 to 3.

The functional principle of this method is schematically represented in short in FIG. 2 by way of the electrodialysis of a common salt solution.

The technical realization of this method employs membrane stacks, the individual membranes being mutually spaced-apart by spacers and the thus formed volumes being separated from one another and from the electrode chamber by means of sealing frames. The alternate use of cation and anion exchange membranes results in an enrichment of ions in the so-called concentrate cycle and an accordingly large decrease of charge carriers in the so-called diluate cycle.

The pilot tests were carried out using a membrane electrolysis cell, stack type 36, with 36 cm$^2$ effective membrane surface area/membrane, 10 cell pairs, a total of 0.0756 m$^2$ eff. membrane surface area.

3.3 Results and Discussion

In the first phase of the pilot tests (tests 1 and 2), it should have been tested which membranes exhibited separation characteristics that were of advantage to the present issue. Basically, two different types of membranes were examined: on the one hand, regular standard membranes and, on the other hand, a membrane type that renders difficult both the unspecific diffusion of unloaded particles and the migration of higher-molecular electrolytes (such as, for instance, organic anions, free aminoacids, . . . ), so-called low diffusion membranes.

3.3.1 Pilot Test 1

| Sample material | Pressed potato juice of the variety Desiree |
| --- | --- |
| | processed as described under 3.2.1: |
| | sedimentation |
| | microfiltration at 1 μm pore size |
| Electrolytic cell | Stack type 36 |
| | 36 cm$^2$ eff. membrane surface area/membrane |
| Membranes | Standard membranes |
| | 10 cell pairs |
| | total of 0.0756 m$^2$ eff. membrane surface area |

| Solutions at beginning of test | | Volume | Flow rate |
| --- | --- | --- | --- |
| Diluate-side | pressed potato juice | 3 l | 70 l/h |
| Concentrate-side | town water | 3 l | 70 l/h |
| Electrode-flushing | Na$_2$SO$_4$ 8.3 mS/cm | 2 l | 300 l/h |

| Test conditions | constant operating voltage of 21 V |
| --- | --- |
| | pole reversal for 30 seconds every 30 minutes |
| Taking of sample | every 30 minutes |

In order to document the ion migration occurring during the test, representative measuring data such as the current intensity (I, [A]), the conductivities both in the diluate and in the concentrate (Lf, [mS/cm]), and also the pH were detected, on the one hand. For illustration purposes, the conductivities of the diluate and of the concentrate over the total test period are graphically shown in the following Figure.

On the other hand, time-dependent samples (6 samples at intervals of 30 minutes each) were drawn and examined in this pretest for the DOC (measured as NPOC) to be interpreted as the summation parameter for organic components, as already described above (results: Table 3).

TABLE 3

| | Town water mg/l | Test 1 30 min mg/l | Test 1 60 min mg/l | Test 1 90 min mg/l | Test 1 120 min mg/l | Test 1 150 min mg/l | Test 1 180 min mg/l | Sample material mg/l |
| --- | --- | --- | --- | --- | --- | --- | --- | --- |
| DOC | 1.1 | 245 | 576 | 792 | 850 | 1530 | 1450 | 9490 |

With this type of membrane (standard membrane) it was remarkable that the anion exchange membranes were severely contaminated and swollen under seizing. The coating could only be partially rinsed off by regular cleaning procedures.

3.3.2 Pilot Test 2

| Sample material | Pressed potato juice of the variety Desiree |
| --- | --- |
| | processed as described under 3.2.1: |
| | sedimentation and |
| | microfiltration at 1 μm pore size |
| Elektrolytic cell | Stack type 36 |
| | 36 cm$^2$ eff. membrane surface area/membrane |
| Membrane | Low diffusion membrane |
| | 10 cell pairs |
| | total of 0.0756 m$^2$ eff. membrane surface area |

| Solutions at beginning of test | | Volume | Flow rate |
| --- | --- | --- | --- |
| Diluate-side | pressed potato juice | 3 l | 70 l/h |
| Concentrate-side | town water | 3 l | 70 l/h |
| Electrode-flushing | Na$_2$SO$_4$ 8.3 mS/cm | 2 l | 300 l/h |

-continued

| Test conditions | constant operating voltage of 21 V pole reversal for 30 seconds every 30 minutes |
|---|---|
| Taking of sample | every 30 minutes |

Figure 4:
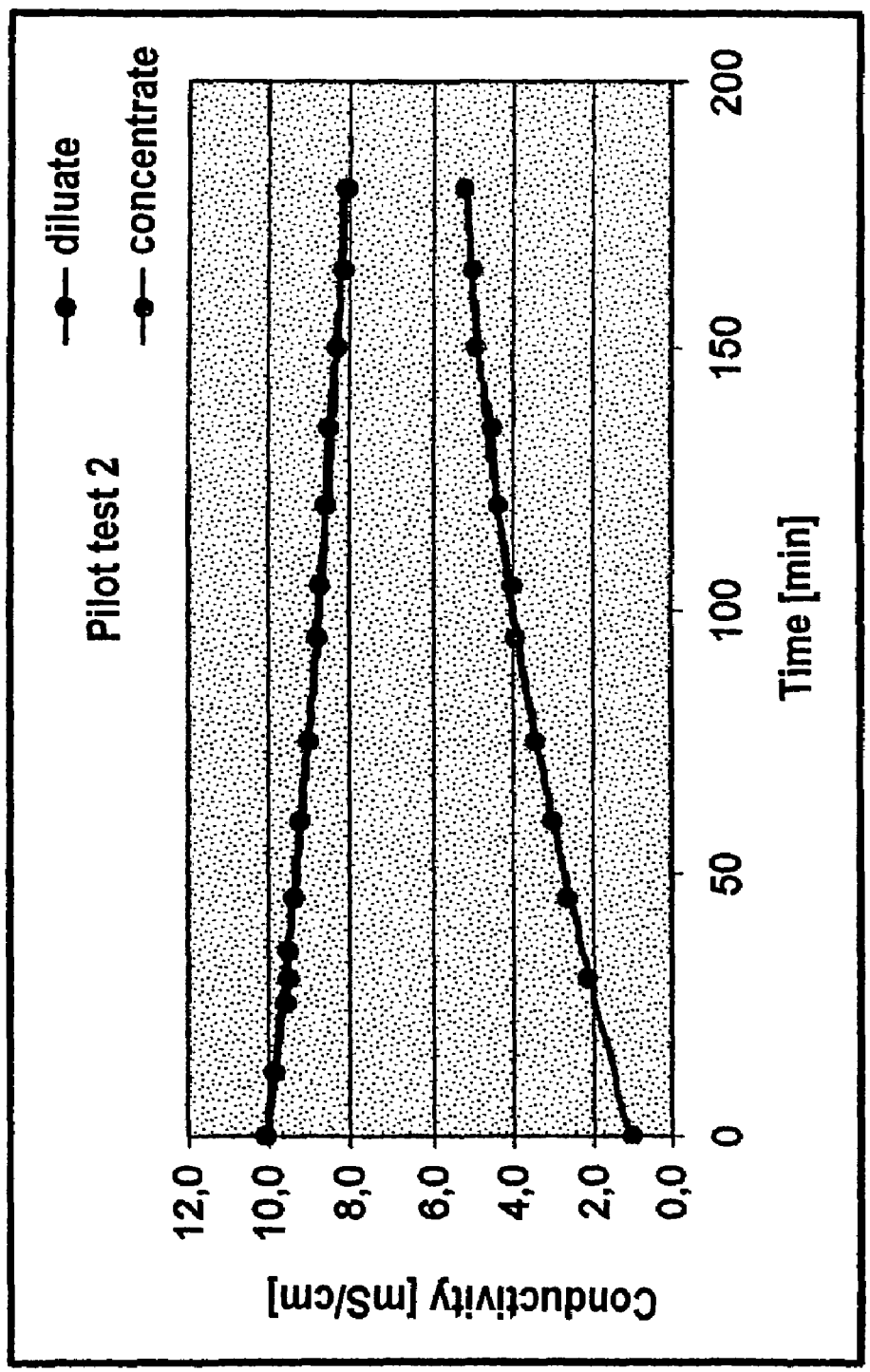

The current intensity, the conductivities both in the diluate and in the concentrate and the pH were detected also in this test. The illustration of the time-dependent changes in the conductivities of the diluate and of the concentrate in FIG. 4 already shows a markedly different profile of the ion migration as compared to the first test.

Time-dependent samples were also drawn in this test at intervals of 30 minutes and examined for their composition. Since the markedly improved aptness of the low diffusion membranes was to be recognized already in the course of the test, an extensive analytics of both the organic components and the inorganic cations and anions was carried out on these samples (cf. Table 4).

TABLE 4

|  | mg/mmol | Town Water mg/l | Test 2 30 min mg/l | mmol/l | Test 2 60 min mg/l | mmol/l | Test 2 90 min mg/l | mmol/l |
|---|---|---|---|---|---|---|---|---|
| Sulfate | 96.06 | 33 | 71 | 0.74 | 95 | 0.99 | 110 | 1.15 |
| Phosphate | 94.97 | 0.03 | 108 | 1.14 | 175 | 1.84 | 239 | 2.52 |
| Chloride | 35.45 | 5.4 | 299 | 8.43 | 364 | 10.27 | 383 | 10.80 |
| Nitrate | 62.01 | 4.3 | <1.0 | n.a. | <1.0 | n.a. | <1.0 | n.a. |
| Malate | 132.10 |  | n.a. | n.a. | n.a. | n.a. | n.a. | n.a. |
| Lactate | 89.08 |  | n.a. | n.a. | n.a. | n.a. | n.a. | n.a. |
| Tartrate | 48.10 |  | n.a. | n.a. | n.a. | n.a. | n.a. | n.a. |
| Citrate | 89.10 |  | n.a. | n.a. | n.a. | n.a. | n.a. | n.a. |
| Isocitrate | 89.10 |  | n.a. | n.a. | n.a. | n.a. | n.a. | n.a. |
| Ascorbate | 175.05 |  | n.a. | n.a. | n.a. | n.a. | n.a. | n.a. |
| DOC |  | 1.1 | 51.9 |  | 83.1 |  | 117.0 |  |
| Σacid-forming |  |  |  | 10.31 |  | 13.10 |  | 14.47 |
| Potassium | 39.10 | 1.3 | 522 | 13.35 | 750 | 19.18 | 942 | 24.09 |
| Magnesium | 24.31 | 8.1 | 12 | 0.49 | 13 | 0.53 | 14 | 0.58 |
| Calcium | 40.08 | 47.7 | 27 | 0.67 | 54 | 1.35 | 42 | 1.05 |
| Sodium | 22.99 | 4.4 | 69 | 3.00 | 75 | 3.26 | 95 | 4.13 |
| Ammonium | 18.04 | <0.01 | n.a. | n.a. | n.a. | n.a. | n.a. | n.a. |
| Iron | 55.84 | 0.005 | 0.64 | 0.01 | 0.70 | 0.01 | 0.43 | 0.01 |
| Zinc | 65.30 |  | 0.15 | 0.00 | 0.08 | 0.00 | 0.09 | 0.00 |
| Manganese | 54.94 | 0.0005 | 1.0 | 0.02 | <0.05 | n.a. | <0.05 | n.a. |
| Copper | 63.54 |  | 0.24 | 0.00 | 0.35 | 0.01 | 0.32 | 0.01 |
| Selenium | 78.90 | 0.0014 | <0.002 | n.a. | <0.002 | n.a. | <0.002 | n.a. |
| Nickel | 58.70 | <0.001 | <0.05 | n.a. | <0.05 | n.a. | 0.09 | 0.00 |
| Chromium | 52.00 | <0.0005 | <0.05 | n.a. | <0.05 | n.a. | <0.05 | n.a. |
| Σbase-forming |  |  |  | 17.55 |  | 24.35 |  | 29.86 |
| Quotient |  |  |  |  |  |  |  |  |
| (Σbase-forming) (Σacid-forming) |  |  |  | 1.70 30 min |  | 1.86 60 min |  | 2.06 90 min |

|  | mg/mmol | Test 2 120 min mg/l | mmol/l | Test 2 150 min mg/l | mmol/l | Test 2 180 min mg/l | mmol/l | Sample material mg/l | mmol/l |
|---|---|---|---|---|---|---|---|---|---|
| Sulfate | 96.06 | 114 | 1.19 | 142 | 1.48 | 153 | 1.59 | 215 | 2.24 |
| Phosphate | 94.97 | 255 | 2.69 | 342 | 3.60 | 376 | 3.96 | 601 | 6.33 |
| Chloride | 35.45 | 360 | 10.16 | 403 | 11.37 | 398 | 11.23 | 270 | 7.62 |
| Nitrate | 62.01 | <1.0 | n.a. | <1.0 | n.a. | <1.0 | n.a. | <1.0 | n.a. |
| Malate | 132.10 | n.a. | n.a. | n.a. | n.a. | n.a. | n.a. | n.a. | n.a. |
| Lactate | 89.08 | n.a. | n.a. | n.a. | n.a. | n.a. | n.a. | n.a. | n.a. |
| Tartrate | 48.10 | n.a. | n.a. | n.a. | n.a. | n.a. | n.a. | n.a. | n.a. |
| Citrate | 89.10 | n.a. | n.a. | n.a. | n.a. | n.a. | n.a. | n.a. | n.a. |
| Isocitrate | 89.10 | n.a. | n.a. | n.a. | n.a. | n.a. | n.a. | n.a. | n.a. |
| Ascorbate | 175.05 | n.a. | n.a. | n.a. | n.a. | n.a. | n.a. | n.a. | n.a. |
| DOC |  | 141.0 |  | 230.0 |  | 351.0 |  | 9490.0 |  |
| Σacid-forming |  |  | 14.03 |  | 16.45 |  | 16.78 |  | 16.18 |
| Potassium | 39.10 | 1030 | 26.34 | 1060 | 27.11 | 1140 | 29.16 | 3110 | 79.54 |
| Magnesium | 24.31 | 14 | 0.58 | 16 | 0.66 | 17 | 0.70 | 215 | 8.84 |
| Calcium | 40.08 | 35 | 0.87 | 26 | 0.65 | <10 | n.a. | 20 | 0.50 |
| Sodium | 22.99 | 103 | 4.48 | 120 | 5.22 | 125 | 5.44 | 2.8 | 0.12 |
| Ammonium | 18.04 | n.a. | n.a. | n.a. | n.a. | n.a. | n.a. | n.a. | n.a. |
| Iron | 55.84 | 0.47 | 0.01 | 0.88 | 0.02 | 0.39 | 0.01 | 4.69 | 0.08 |
| Zinc | 65.30 | 0.06 | 0.00 | 0.06 | 0.00 | <0.05 | n.a. | 2.6 | 0.04 |
| Manganese | 54.94 | <0.05 | n.a. | 0.05 | 0.00 | 0.05 | 0.00 | 1.9 | 0.03 |
| Copper | 63.54 | 0.29 | 0.00 | 0.30 | 0.00 | 0.19 | 0.00 | 1.20 | 0.02 |

TABLE 4-continued

| | | | | | | | | | |
|---|---|---|---|---|---|---|---|---|---|
| Selenium | 78.90 | <0.002 | n.a. | <0.002 | n.a. | <0.002 | n.a. | <0.002 | n.a. |
| Nickel | 58.70 | 0.06 | 0.00 | 0.06 | 0.00 | <0.05 | n.a. | 2.6 | 0.04 |
| Chromium | 52.00 | <0.05 | n.a. | <0.05 | n.a. | <0.05 | n.a. | <0.05 | n.a. |
| Σbase- forming Quotient | | | 32.29 | | 33.66 | | 35.30 | | 89.23 |
| (Σbase-forming) (Σacid-forming) | | | 2.30 120 min | | 2.05 150 min | | 2.10 180 min | | 5.51 Sample material |

The fouling process observed in the first test, i.e., the obstruction of the anion exchange membranes could only be observed to a far less extent when using low diffusion membranes. Furthermore, this obstruction was readily removable by conventional cleaning methods, and the deforming swelling process could not be observed at all.

3.3.3 To Sum Up, the Results of the First Two Tests Demonstrated the Following:

The low diffusion membranes used in the second test exhibit an enhanced separation behavior for the issue in question, since they render the transportation of undesired organic portions into the concentrate significantly more difficult. The DOC as the summation parameter for these portions amounts to 1450 mg/l after a test period of 180 minutes when using standard membranes as opposed to 351 mg/l after the same test period under otherwise identical conditions when using low diffusion membranes. For comparison, that of the pressed potato juice used was 9490 mg/l.

Also in respect to the undesired fouling behavior, low diffusion membranes are to be clearly preferred. On the one hand, no deformations by swelling processes are to be observed and, on the other hand, obstruction of the membranes occurs to a far lower extent.

Considering the detailed analysis of the ionogenic substances in the concentrate of the second test, the following facts have become apparent:

The migration of inorganic anions largely corresponds to the pattern expected according to the theoretical background that monovalent ions migrate faster than bivalent ones and bivalent ions migrate faster than trivalent ones. As compared to the pressed potato juice used, 62% phosphate and 70% sulfate had migrated after a test period of 180 minutes. By contrast, the detected chloride concentrations largely exceed those expected, being even higher than those present in the original pressed potato juice, namely 3.6 mmol/l in excess. As will be set out in the following chapter relating to cations, a likewise significant excess of sodium (5.3 mmol/l) is to be detected in the concentrate. These facts, which appear to be in contradiction at first sight, can however be explained by an ion exchange occurring at the membranes used. According to the manufacturer's information, the ion exchange capacity of the membranes amounts to 1.5 mmol/g dry membrane. Under the assumption that a membrane has a dry weight of about 1 gram and 10 cation and anion membranes are each used in the test array, a potential introduction of the counterions sodium and chloride bound to the membrane is each possible at an extent of 15 mmol and, considering the overall concentrate volume of 3 liters, even in the order of the detected excess. This phenomenon of the ions, bound to the ion exchanger surfaces by the manufacturer, being detached is conceivable under the absolutely plausible assumption that the binding sites have been occupied in the course of the test by possible higher-molecular portions to be recognized as coatings just optically, too.

Considering the migration behavior of the cations, it is noted—in addition to the already discussed excess of sodium—that all of the cations are significantly hampered in their diffusion by the membrane. For instance, of potassium, which is actually supposed to migrate relatively completely because of its mono-valency, only 37% is present in the concentrate. With higher-valent cations—although primarily with the value-determining ions calcium and magnesium, yet definitely also with the trace elements iron, copper, manganese, nickel and zinc—the ratios are even more drastic. All of the detectable calcium and magnesium originates from the town water used at the beginning of the test, apparently reflecting the fact that the monovalent cations migrated poorly and the polyvalent cations did not migrate at all.

Phenomena of this kind are known in electrodialysis and even sought in special cases. Specifically coated membranes are, for instance, employed as "selective ion exchange membranes" in order to selectively separate monovalent from polyvalent ions. Since in our test the separation properties of the membranes were apparently changed in a similar manner through obstruction by accompanying substances from the pressed potato juice, an additional filtration step was piloted for the following test to prepurify the juice, namely an ultrafiltration at an exclusion limit of 1000 Da.

3.3.4 Pilot Test 3

As already pointed out, the first two pilot tests proved that the pressed potato juice so far prepurified by sedimentation and microfiltration at a pore size of 1 μm has to be further treated in order to avoid as largely as possible the undesired fouling phenomenon that changes the separation properties.

Consequently, the sample material for the subsequent electrodialytical pilot test was prefiltered by ultrafiltration at an exclusion limit of 1000 Da.

A pretest to said filtration step was carried out in an agitation cell—as already described above—in order to find out whether value-determining ions would be lost by this method step. The potential chance of a loss of, above all, the bivalent cations magnesium and calcium by complexing with molecules having visceral OH groups as occur in carbohydrates was to be verified.

However, since the results clearly indicated that no value-determining electrolyte was lost (as is apparent from the Table of results from the third pilot test (Table 5)), the amount required for an additional electrodialytical step was filtered in a plate module likewise equipped with the above-mentioned polysulfone membranes at an exclusion limit of 1000 Da.

Even with this membrane method, the fouling phenomena already observed during electrodialysis were discovered. Periodic back flushing during filtration was necessary.

The third electrodialytical pilot test was finally carried out as indicated below using the filtrate derived from ultrafiltration, under optimized general conditions of the first two tests (using low diffusion membranes, period pole reversal):

| Sample material | Pressed potato juice of the variety Desiree processed as described under 3.2.1 and 3.2.2: sedimentation and microfiltration at 1 μm pore size ultrafiltration at an exclusion limit of 1000 Da |
|---|---|
| Electrolytic cell | Stack type 36 36 cm² eff. membrane surface area/membrane |
| Membrane | Low diffusion membrane 10 cell pairs total of 0.0756 m² eff. membrane surface area |

| Solutions at beginning of test | | Volume | Flow rate |
|---|---|---|---|
| Diluate-side | pressed potato juice | 2 l | 75 l/h |
| Concentrate-side | CD water | 2 l | 75 l/h |
| Electrode-flushing | $Na_2SO_4$ 8.3 mS/cm | 2 l | 200 l/h |

| Test conditions | constant operating voltage of 21 V pole reversal for 30 seconds every 30 minutes |
|---|---|
| Test period | 180 minutes |

Figure 5:
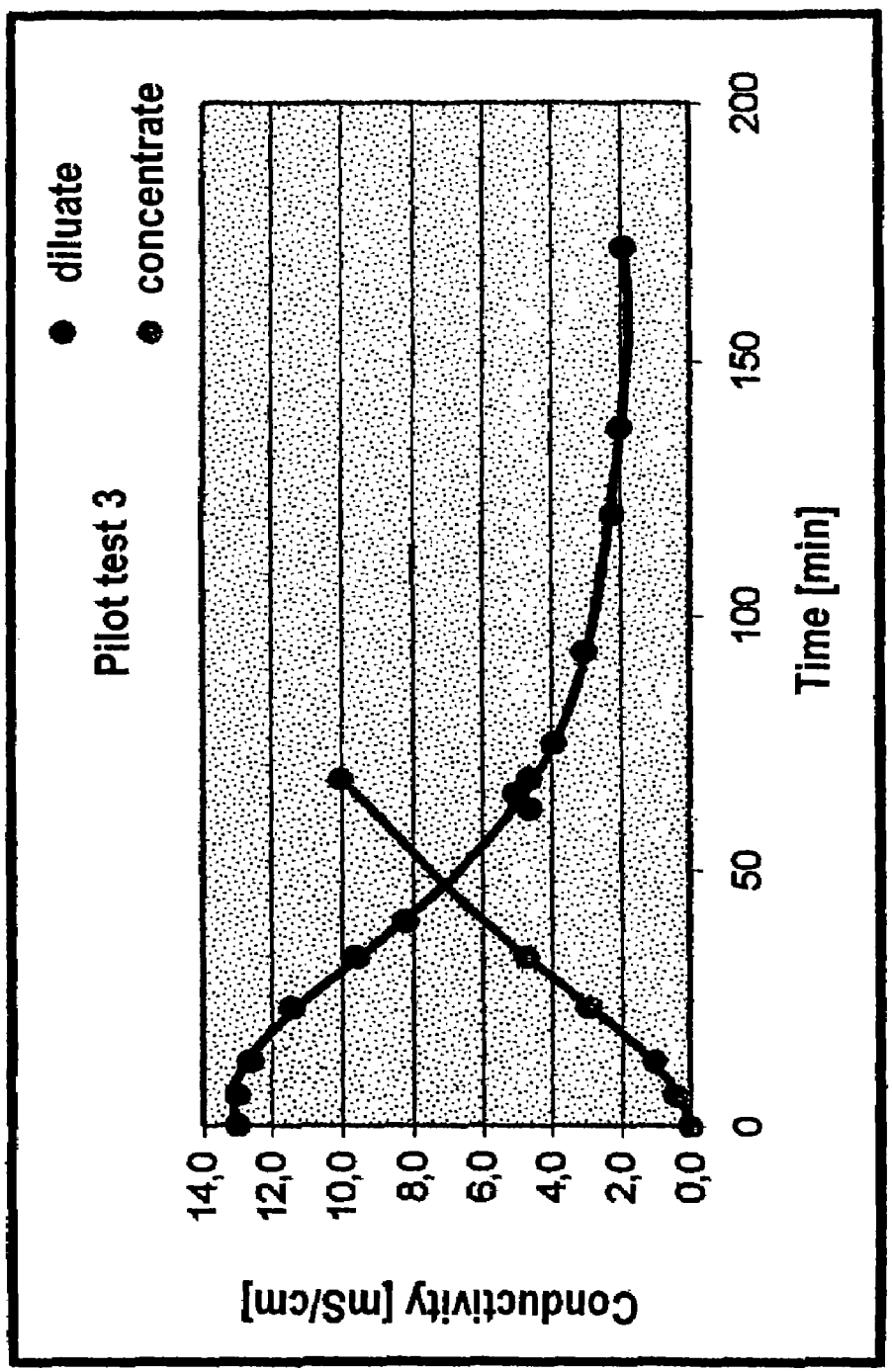

As in the previous tests, also here the current intensity and the conductivities both in the diluate and in the concentrate were detected, the latter being graphically illustrated (FIG. 5).

What was striking about this test was the sigmoid curve as compared to the two other tests, which rather resulted in hyperbolic courses. This phenomenon can be explained by the water used on the concentrate side at the beginning of the test, which had a different quality and conductivity. In tests 1 and 2, dialyzation was run against town water having the ion composition known from the analysis, for which reason some conductivity was present already at time 0. By contrast, the last test was started with CD (completely demineralized) water, which showed no conductivity at all at the beginning of the test, thus leading to the retarded onset of electrodialysis to be graphically observed.

TABLE 5

| | | Test 3 180 min diluate | | Test 3 180 min concentrate | | % (concentrate/ diluate) | Sample material ultrafiltered | | Test 2 180 min concentrate | |
|---|---|---|---|---|---|---|---|---|---|---|
| | mg/mmol | mg/l | mmol/l | mg/l | mmol/l | | mg/l | mmol/l | mg/l | mmol/l |
| Sulfate | 98.06 | 66 | 0.69 | 189 | 1.97 | 74.1 | 241 | 2.51 | 153 | 1.59 |
| Phosphate | 94.97 | 141 | 1.48 | 520 | 5.48 | 78.7 | 625 | 6.58 | 376 | 3.96 |
| Chloride | 35.45 | 36 | 1.02 | 513 | 14.47 | 93.4 | 298 | 8.41 | 398 | 11.23 |
| Nitrate | 62.01 | 1.7 | 0.03 | 3 | 0.05 | 63.8 | <1.0 | n.a. | <1.0 | n.a. |
| Malate | 132.10 | 69 | 0.52 | 737 | 5.58 | 91.4 | n.a. | n.a. | n.a. | n.a. |
| Lactate | 89.08 | <1 | n.a. | <1 | n.a. | n.a. | n.a. | n.a. | n.a. | n.a. |
| Tartrate | 148.10 | <1 | n.a. | 36 | 0.24 | n.a. | n.a. | n.a. | n.a. | n.a. |
| Citrate | 189.10 | 281 | 1.49 | 452 | 2.39 | 61.7 | n.a. | n.a. | n.a. | n.a. |
| Isocitrate | 189.10 | 67 | 0.35 | 166 | 0.88 | 71.2 | n.a. | n.a. | n.a. | n.a. |
| Ascorbate | 175.05 | 0.4 | 0.00 | 0.3 | 0.00 | 42.9 | n.a. | n.a. | n.a. | n.a. |
| DOC | | 4760 | | 4000 | | 45.7 | n.a. | | 351.0 | |
| Σacid-forming inorganic | | | 3.21 | | 21.96 | | | 17.50 | | 16.78 |
| Σacid-forming total | | | 5.58 | | 31.05 | | | | | |
| Potassium | 39.10 | 516 | 13.20 | 3500 | 89.51 | 87.2 | 3890 | 99.49 | 1140 | 29.16 |
| Magnesium | 24.31 | 36 | 1.48 | 210 | 8.64 | 85.4 | 272 | 11.19 | 17 | 0.70 |
| Calcium | 40.08 | <10 | n.a. | 72 | 1.80 | 100.0 | 124 | 3.09 | <10 | n.a. |
| Sodium | 22.99 | 37 | 1.61 | 189 | 8.22 | 83.6 | 15.6 | 0.68 | 125 | 5.44 |
| Ammonium | 18.04 | n.a. | n.a. | n.a. | n.a. | n.a. | n.a. | n.a. | n.a. | n.a. |
| Iron | 55.84 | 24 | 0.43 | 57 | 1.02 | 70.4 | 0.44 | 0.01 | 0.39 | 0.01 |
| Zinc | 65.30 | 0.98 | 0.02 | 2.36 | 0.04 | 70.7 | 2.5 | 0.04 | <0.05 | n.a. |
| Manganese | 54.94 | 0.33 | 0.01 | 1.69 | 0.03 | 83.7 | 1.29 | 0.02 | 0.05 | 0.00 |
| Copper | 63.54 | 0.65 | 0.01 | 0.2 | 0.00 | 23.5 | 0.63 | 0.01 | 0.19 | 0.00 |
| Selenium | 78.90 | <0.002 | n.a. | <0.002 | n.a. | n.a. | 0.002 | n.a. | <0.002 | n.a. |
| Nickel | 58.70 | 1.03 | 0.02 | 0.26 | 0.00 | 20.2 | 0.06 | 0.00 | <0.05 | n.a. |
| Chromium | 52.00 | 0.72 | 0.01 | 0.24 | 0.00 | 25.0 | <0.05 | n.a. | <0.05 | n.a. |
| Σbase-forming | | | 16.78 | | 109.27 | | | 114.53 | | 35.30 |
| Ratio (Σbase-forming) to | | | | | | | | | | |
| (Σacid-forming inorganic) | | | 5.22 | | 4.98 | | | 6.55 | | 2.10 |
| (Σacid-forming total) | | | 3.01 | | 3.52 | | | | | |

The concentrate of this pilot test, on the one hand, was analyzed for its ion composition and, on the other hand, was evaporated by surface rotary evaporation. Under the test conditions of the laboratory plant (40° C. and vacuum up to 30 mbar) 9.96 g amorphous product were obtained from 360 ml concentrate.

In this context, it should be noted that the present drying method chosen for laboratory scale will naturally be inadequate for large-scale application. In that case, a method such as, for instance, spray-drying or drum-drying is, of course, to be piloted and optimized.

Upon consideration of the analytical results of the pilot test 3, which includes the additional prepurification of the pressed potato juice through ultrafiltration prior to electrodialysis, the following facts will become apparent:

The problems occurring in the second test due to the obstruction of the ion exchange membranes could be largely overcome by prepurifying the juice through ultrafiltration at an exclusion limit of 1000 Da. The higher-molecular portions which, in the first two tests, led to the problematic fouling phenomena and the thus caused changes in the separation properties of the membranes severely affecting cation migration apparently were efficiently removed from the sample matrix by this method step.

Furthermore, unlike in the second pilot test, also the problems of ion exchange and the thus caused detachment of the counter ions chloride and sodium from the membranes on account of matrix components of the sample were no longer observed due to the ultrafiltration of the juice. The migration of the inorganic anions in this test much rather meets the expectations. Thus, for instance, 74% sulfate, 79% phosphate and 93% chloride migrated. Also the organic anions migrated as a function of their charges and sizes; 91% malate, the smallest one of the anions examined, 62% citrate, 72% isocitrate and 42% ascorbate migrated.

Naturally, the enhanced ion migration also had effects on the organic components of the sample matrix included in the summation parameter of the DOC. Thus, the DOC in this case is 4000 mg/l in the concentrate and hence clearly higher than in the second pilot test. In this context, it should however be noted that this value also includes the organic anions quantified in detail. The components not detected qualitatively and quantitatively, yet to be likewise found in the concentrate and contributing to this summation parameter are supposed to comprise above all aspartate and glutamate.

Considering the migration behavior of the cations, it is clearly apparent that the problems involved in the second test due to the fouling behavior have been overcome by the additional method step of ultrafiltration. The value-determining cations for the product to be developed migrate in an extremely satisfactory manner by the combination of method steps finally applied. Even 85% and 100%, respectively, of the bivalent cations magnesium and calcium migrate. 87% potassium, 84% sodium and between 70 and 84% of the quantitatively less dominating ions like iron, zinc and manganese migrate.

This extremely satisfying improvement in the electrodialytical performance is also reflected by the quotients from the sum of base-forming and acid-forming electrolytes defined already in the beginning. Comparing, for instance, the quotients between the second and third tests, an increase from 2.10 to 4.98, i.e., an increase by 237% was achieved by this innovation. In this respect, it should be noted that the above-mentioned quotients are based on the inorganic anions, since the organic anions were not analyzed in detail in test 2.

When comparing the quotient that takes into account also the analyzed organic anions, our end product exhibits a value of 3.52 as against the non-processed potato juice, which has a value of 1.55 in the case of the variety Desiree. Thus, an increase of 227% was achieved here.

The invention claimed is:

1. A method for the preparation of a potato juice product, comprising:
   obtaining a pressed potato juice having a ratio of base-forming to acid-forming components of at least 1.5;
   separating fiber or starch residues from the juice by filtration through a microfilter to produce a microfiltrate; and
   performing electrodialysis on the microfiltrate to produce an electrodialysate.

2. The method of claim 1, wherein fiber or starch residues are separated through ultrafiltration, to product an ultrafiltrate.

3. The method of claim 2, wherein electrodialysis is performed on the ultrafiltrate.

4. The method of claim 1, further comprising drying the electrodialysate.

5. The method of claim 4, wherein drying comprises adding a silicate-containing carrier substance to the electrodialysate.

6. The method of claim 5, wherein drying comprises adding highly disperse silicon dioxide to the electrodialysate.

7. The method of claim 4, wherein the drying comprises spray-drying or drum-drying.

8. The method of claim 1, further comprising adding a stabilizer to the pressed potato juice.

9. The method of claim 8, wherein the stabilizer is a natural antioxidant.

10. The method of claim 9, wherein the natural antioxidant is lemon juice or a lemon juice product.

11. The method of claim 1, wherein obtaining the pressed potato juice comprises pressing one or more potatoes.

12. The method of claim 1, wherein the ratio of base-forming to acid-forming components is above 3.5.

13. The method of claim 1, wherein the pressed potato juice is from at least one of the Desiree or Ackersegen potato varieties.

14. The method of claim 2, wherein the ultrafiltration is carried out using an ultrafilter having a cut-off of below 100,000 Da.

15. The method of claim 14, wherein the ultrafilter has a cut-off of below 10,000 Da.

16. The method of claim 15, wherein the ultrafilter has a cut-off of approximately 1,000 Da.

17. The method of claim 1, wherein the electrodialysis is carried out using a membrane stack.

18. The method of claim 1, wherein the potato juice product obtained is supplemented with at least one additional agent.

19. The method of claim 18, wherein the at least one additional agent is a vegetable or fruit juice, a stabilizer, a flavoring or coloring agent, a thickening agent, or a reconstitution or electrolytic agent.

20. The method of claim 19, wherein the at least one additional agent is a stabilizer further defined as a natural antioxidant.

21. The method of claim 19, wherein the at least one additional agent is a natural flavoring or coloring agent.

22. The method of claim 18, wherein the at least one additional agent is a vitamin, mineral substance, trace element, or secondary plant substance.

23. The method of claim 1, further comprising administering the potato juice product to a subject.

24. The method of claim 23, wherein the subject is a human.

25. A potato juice product obtained by:
   obtaining a pressed potato juice;
   separating fiber or starch residues from the juice by filtration through a microfilter to produce a microfiltrate; and
   performing electrodialysis on the microfiltrate to produce an electrodialysate having a ratio of base-forming to acid-forming components of at least 2.5.

26. The potato juice product of claim 25, further defined as comprising 1000 mg/l of organic components, determined as non-purgeable organic carbon.

27. The potato juice product of claim 26, comprising 2000 mg/l of organic components, determined as non-purgeable organic carbon.

28. The potato juice product of claim 27, comprising 4000 mg/l of organic components, determined as non-purgeable organic carbon.

29. The potato juice product of claim 25, wherein the ratio of base-forming to acid-forming components is above 4.

30. The potato juice product of claim 29, wherein the ratio of base-forming to acid-forming components is above 6.

31. A method of controlling acid-base balance in a subject comprising:
   obtaining a potato juice product via a method comprising:
      obtaining a pressed potato juice;
      separating fiber or starch residues from the juice by filtration through a microfilter to produce a microfiltrate; and
      performing electrodialysis on the microfiltrate to produce an electrodialysate having a ratio of base-forming to acid-forming components of at least 2.5; and
   administering the potato juice product to a subject.

32. The method of claim 31, wherein the subject is a human.

* * * * *